United States Patent [19]
Omure et al.

[11] Patent Number: 5,561,172
[45] Date of Patent: Oct. 1, 1996

[54] METHOD OF PRODUCING RIGID POLYURETHANE FOAMS

[75] Inventors: Yukio Omure; Tatsumi Tsuchiya, both of Settsu; Kiyohiro Yuge, Yawata; Hitoshi Muramatsu, Chiba, all of Japan

[73] Assignee: Daikin Industries, Ltd., Osaka, Japan

[21] Appl. No.: 290,701

[22] PCT Filed: Feb. 12, 1993

[86] PCT No.: PCT/JP93/00175

§ 371 Date: Nov. 21, 1994

§ 102(e) Date: Nov. 21, 1994

[87] PCT Pub. No.: WO93/16122

PCT Pub. Date: Aug. 19, 1993

[30] Foreign Application Priority Data

Feb. 14, 1992 [JP] Japan .................................. 4-028500

[51] Int. Cl.⁶ .................................................. C08J 9/06
[52] U.S. Cl. ......................... 421/131; 521/155; 521/159; 521/170; 521/174; 528/76; 528/85; 560/330; 560/331; 560/332
[58] Field of Search .................... 521/131, 155, 521/159, 170, 174; 528/76, 85; 560/330, 331, 332

[56] References Cited

U.S. PATENT DOCUMENTS

| | | | |
|---|---|---|---|
| 4,652,589 | 3/1987 | Simroth et al. | 521/137 |
| 4,904,704 | 2/1990 | Nafziger et al. | 521/156 |
| 5,135,680 | 8/1992 | Crooker et al. | |
| 5,216,042 | 6/1993 | Daussin et al. | 521/160 |

FOREIGN PATENT DOCUMENTS

| | | |
|---|---|---|
| 0401722 | 6/1990 | European Pat. Off. |
| 0508449 | 4/1992 | European Pat. Off. |
| 93/00395 | 6/1992 | WIPO |

Primary Examiner—James J. Seidleck
Assistant Examiner—Duc Truong
Attorney, Agent, or Firm—Larson and Taylor

[57] ABSTRACT

A primary object of the invention is to provide a method of producing rigid polyurethane foams using 1,1-dichloro-1-fluoroethane (HCFC-141b) as the blowing agent while substantially avoiding the formation of decomposition products from HCFC-141b. The above object can be achieved by a method of producing rigid polyurethane foams which comprises reacting a polyol with an organic polyisocyanate for foaming in the presence of HCFC-141b and a stabilizer therefor and in the presence of an organic metal catalyst and/or an imidazole compound catalyst and by the thus-produced rigid polyurethane foams.

16 Claims, No Drawings

METHOD OF PRODUCING RIGID POLYURETHANE FOAMS

TECHNICAL FIELD

This invention relates to a method of producing rigid polyurethane foams which comprises using, as the blowing agent, 1,1-dichloro-1-fluoroethane (hereinafter referred to as HCFC-141b) containing a stabilizer and, as the catalyst, an organic metal catalyst and/or an imidazole compound catalyst to thereby control the decomposition of HCFC-141b, and to the thus-obtained rigid polyurethane foams substantially free of HCFC-141b-derived decomposition products.

BACKGROUND ART

Rigid polyurethane foams are good insulating materials and are excellent in moldability and processability. Therefore, they are widely used in various; fields, for example as insulating materials for refrigerators, buildings, low-temperature warehouses, storage tanks, refrigerator ships, pipes and so forth. They have been improved in thermal conductivity year by year. At present, they can have a thermal conductivity as low as about 0.015 W/mK on the commercial product level and thus show the best insulator performance among heat insulating materials used at around normal temperature. However, the requirement that the insulating materials should have a still lower thermal conductivity is increasing with the recent request for much more energy saving.

In producing rigid polyurethane foams, the so-called one-shot process is generally used which comprises mixing a composition (A) comprising, as main components thereof, a polyol, a catalyst, a foam controlling agent (cell stabilizer) and a blowing agent with a composition (B) comprising, as a main component thereof, an organic polyisocyanate and thus causing the foaming process and curing process to proceed in parallel for foam formation.

A typical example of the blowing agent used in such rigid polyurethane foam production is trichlorofluoromethane (R-11). R-11 is often used in combination with water, which is a chemical blowing agent capable of reacting with isocyanates to generate carbon dioxide. However, the conventional chlorofluorocarbon (CFC) blowing agents, typically R-11, are chemically stable and therefore, as heretofore pointed out, can diffuse far into the stratosphere and destroy the ozone layer. The result would be that ultraviolet radiation from the sun be not absorbed in the ozone layer but reach the surface of the earth, causing skin ,cancer and so on. Such is now a serious global-scale environmental problem. Therefore, the use of CFCs has been restricted since 1989. Of course, the use of R-11 in urethane foam production is now under control.

Accordingly, various investigations have been made in search of blowing agents capable of serving as alternatives for CFC gases. Thus, HCFC-141b, for instance, has been nominated as a candidate alternative for CFCs.

However, it is already known that when HCFC-141b is used, for instance, as a blowing agent in producing rigid polyurethane foams by the conventional method, 1-chloro-1-fluoroethane (hereinafter referred to as HCFC-151a) is formed as a result of reduction and/or 1-chloro-1-fluoroethene (hereinafter referred to as HCFC-1131a) as a result of dehydrochlorination. The physical properties and toxicities of these decomposition products are still unknown in many aspects, hence might be hazardous to the environment.

DISCLOSURE OF THE INVENTION

Accordingly it is a primary object of the invention to provide a method of producing rigid urethane foams substantially without allowing the decomposition product formation from HCFC-141b.

In view of such technological problems as mentioned above, the present inventors made extensive investigations to develop a method of producing rigid polyurethane foams by which no decomposition products are formed from HCFC-141b and, as a result, found that when a polyol is reacted with an organic polyisocyanate for foaming in the presence of 1,1-dichloro-1-fluoroethane as the blowing agent and a stabilizer therefor and in the presence of an organic metal catalyst and/or an imidazole compound catalyst, rigid polyurethane foams can be obtained without formation of any decomposition product from HCFC-141b. This finding has now led to completion of the present invention.

Thus the invention consists in a method of producing rigid polyurethane foams which comprises reacting a polyol with an organic polyisocyanate for foaming in the presence of 1,1-dichloro-1-fluoroethane as a blowing agent and a stabilizer therefor and in the presence of an organic metal catalyst and/or an imidazole compound catalyst.

The polyol to be used in the practice of the invention may be any of those polyols that are generally used in the production of rigid polyurethane foams, for example polyether polyols containing 2 to 8 functional groups and having a hydroxyl value of about 300 to 600 mg KOH/g, polyester polyols containing 2 to 4 functional groups and having a hydroxyl value of about 250 to 500 mg KOH/g, and the like. Phenol resins having reactive methylol groups, for instance, may also be used. As particularly preferred examples among such polyols, there may be mentioned, among others, polyether polyols derived from trimethylolpropane, sorbitiol, o- or m-tolylenediamine or the like by addition of ethylene oxide and/or propylene oxide and having a hydroxyl value of about 300 to 600 mg KOH/g.

The organic polyisocyanate to be used in the practice of the invention is preferably polymethylenepolyphenyl isocyanate (hereinafter referred to as c-MDI) representable by the general formula

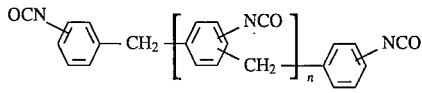

wherein n is an integer of 0 through 6, and/or tolylene diisocyanate (hereinafter referred to as TDI). c-MDI and/or TDI may be used in the form of a prepolymer with a hydroxyl-containing compound or in combination with some other organic polyisocyanate. As said hydroxyl-containing compound, there may be mentioned, for instance, monohydric alcohols and phenols containing one functional group and having a molecular weight of about 32 to 300; polyols containing 2 or 3 functional groups and having a molecular weight of about 62 to 600, and so on. Specific examples are monohydric alcohols such as methanol, ethanol, n-butanol, ethylene glycol monomethyl ether and diethylene glycol monomethyl ether; phenols such as phenol, o-, m- and p-cresol; diols such as ethylene glycol, diethylene glycol, propylene glycol, 1,4-butanediol and 1,6-hexanediol; triols such as glycerol and trimethylolpropane; and, further, bi- or trifunctional polyether polyols, polyester polyols, etc. As examples of the above-mentioned bi- or trifunctional polyether polyols, there may be mentioned polyether polyols obtainable by polymerizing one or more alkylene oxides, such as ethylene oxide, propylene oxide, butylene oxide, etc., using a diol, such as ethylene glycol, propylene glycol or bisphenol A, a triol, such as glycerol or trimethylolpropane, or the like as an initiator. As examples of the above-mentioned bi- or trifunctional polyester polyols, there may be mentioned polyester polyols obtainable by condensation of a polyol, such as ethylene glycol, diethylene glycol, 1,4-butanediol or trimethylolpropane, with a dicarboxylic acid, such as adipic acid, succinic acid, maleic anhydride or phthalic acid. Mention may further be made of polyhydric alcohols such as methyl glucoside, sucrose, sorbitol, dulcitol, etc., as well as polyether polyols obtainable by polymerization of one or more alkylene oxides, such as ethylene oxide, propylene oxide, butylene oxide, etc., using any of such polyhydric alcohols as an initiator.

In accordance with the invention, HCFC-141b is used as a blowing agent. This may be used in combination with water as a chemical blowing agent. The amount of blowing agent may suitably be selected depending on the density of the desired rigid polyurethane foam. Generally, however, the blowing agent is used in an amount of about 1 to 100% by weight on the polyol basis.

As the stabilizer to be used for the blowing agent in accordance with the invention, there may be mentioned, among others, nitro compounds such as nitroalkanes containing 1 to 8 carbon atoms, nitrobenzene, dinitrobenzene, trinitrobenzene, halogenated nitrobenzenes, nitroanisole, nitrostyrene, nitrophenol, nitrocatechol, etc.; alkenyl-containing compounds containing at least one double bond, such as hexadiene, allene, butadiene, isoprene, pentadiene, β-myrcene, isopropenyltoluene, diisopropenylbenzene, alloocimene, etc.; epoxy-containing compounds such as 1,2-butylene oxide, isobutylene oxide, glycidyl allyl ether, glycidyl phenyl ether, glycidyl p-isopropenylphenyl ether, glycidyl p-nitrophenyl ether, 1,3-butadienyl glycidyl ether, glycidyl acrylate, glycidyl furancarboxylate, N,N-diglycidylaniline, etc.; acrylic acid esters and methacrylic acid esters, such as 2-hydroxyethyl methacrylate, diethylene glycol monomethyl methacrylate, methoxypolyethylene glycol monoethyl methacrylate, etc.; and phenols such as 2,6-di-tert-butyl-p-cresol, thymol, p-tert-butylphenol, eugenol, isoeugenol, butylated hydroxyanisole, tert-butylcatechol, 2,5-di-tert-butylhydroquinone, etc. The compounds mentioned above may be used singly, or at least one of such nitro compounds may be used in combination with at least one compound selected from among such alkenyl-containing compounds containing at least one double bond, epoxy-containing compounds, acrylic acid esters, methacrylic acid esters and phenols as mentioned above.

The amount of stabilizer may vary depending on the foaming conditions and other factors but suitably lies within the range of 0.1 to 10% by weight, more preferably within the range of 0.3 to 6% by weight, on the blowing agent basis. A stabilizer amount less than 0.1% by weight based on the blowing agent basis may sometimes fail to effectively prevent the formation of HCFC-151a from HCFC141b, whereas a stabilizer amount exceeding 10% by weight on the blowing agent basis may adversely affect the characteristics of foams, hence may fail, in certain instances, to produce substantial improvement. The stabilizer or stabilizers may be dissolved beforehand in HCFC-141b or may be added on the occasion of foaming independently of the blowing agent.

In the practice of the invention, the organic polyisocyanate is used in an amount within the range such that the NCO/OH ratio in relation to the polyol amounts to 1.0 to 3.0.

In the practice of the invention, any of the conventional foam controlling agents may be used. Thus, use as the foam controlling agent may be made of silicone type surfactants such as organopolysiloxanes, organopolysiloxane-polyoxyalkylene copolymers, polyalkenylsiloxanes having polyoxyalkylene side chains, etc. as well as cationic, anionic and nonionic surfactants. Generally, the foam controlling agent is used in an amount of about 0.2 to 10% by weight on the polyol basis.

In accordance with the invention, foaming is effected using an organic metal catalyst and/or an imidazole compound catalyst. As the organic metal catalyst, there may be mentioned, for example, such organic metal compounds as stannous octoate, dibutyltin dilaurate, lead octylate, etc. The imidazole compound catalyst includes, among others, imidazole, 1-methylimidazole, 1,2-dimethylimidazole, 1-methyl-2-propylimidazole, 1-methyl-2-isobutylimidazole, 1-n-butyl-2-methylimidazole, etc. The catalyst mentioned above may be used in a mixture of two or more of such compounds. The catalyst is used in an amount of about 0.01 to 20% by weight on the organic polyisocyanate basis.

The means for producing rigid polyurethane foams from the raw materials mentioned above is not limited to any particular one provided that it contains an apparatus suited for uniform mixing of the raw materials. Thus, for example, desired rigid polyurethane foams can be readily obtained by mixing said raw materials uniformly using a small-size laboratory mixer, a foaming machine, or the like.

EFFECTS OF THE INVENTION

In accordance with the invention, rigid polyurethane foams can be produced by the conventional procedure.

When, in accordance with the invention, stabilizer-containing HCFC-141b is used as a blowing agent and an organic metal catalyst and/or an imidazole compound catalyst as a catalyst, rigid polyurethane foams can be obtained by the conventional procedure without causing decomposition of HCFC-141b. Therefore, the rigid polyurethane foams obtained by the method of the invention are substantially free of HCFC-151a formable from HCFC-141b by reduction reaction and of HCFC-1131a formable from HCFC-141b by dehydrochlorination, among others.

BEST MODES FOR CARRYING OUT THE INVENTION

The following comparative examples and working examples illustrate the present invention in further detail.

In the examples, the following raw materials were used:
Polyol: o-Tolylenediamine-based polyether polyol with a hydroxyl value of 400 mg KOH/g
Cell controlling agent: Silicone type cell controlling agent SH-193, obtained from Toray Silicone Kabushiki Kaisha
Catalyst A: Tetramethylhexamethylenediamine
Catalyst B: Organic metal catalyst; dibutyltin dilaurate (TL-1000), obtained from Yoshitomi Pharmaceutical Industries
Catalyst C: Imidazole compound catalyst; 1-n-butyl-2-methylimidazole
Blowing agent: HCFC-141b
Stabilizer A: Nitrobenzene
Stabilizer B: p-Isopropenyltoluene
Stabilizer C: 2,6-Di-tert-butyl-p-cresol
Stabilizer D: Isobutylene oxide
Organic polyisocyanate: c-MDI

TABLE 1

|  |  | Comparative Example | | | Example | | | | | | |
| --- | --- | --- | --- | --- | --- | --- | --- | --- | --- | --- | --- |
|  |  | 1 | 2 | 3 | 1 | 2 | 3 | 4 | 5 | 6 | 7 |
| Raw materials (parts by weight) | polyol | 100 | 100 | 100 | 100 | 100 | 100 | 100 | 100 | 100 | 100 |
|  | Cell controlling agent | 2 | 2 | 2 | 2 | 2 | 2 | 2 | 2 | 2 | 2 |
|  | Catalyst A | 2 |  |  |  |  |  |  |  |  |  |
|  | Catalyst B |  | 0.3 | 0.7 |  | 0.3 | 0.3 | 0.3 | 0.3 | 0.3 | 0.3 |
|  | Catalyst C |  | 2.7 | 2.3 | 3 | 2.7 | 2.7 | 2.7 | 2.7 | 2.7 | 2.7 |
|  | Blowing agent | 30 | 30 | 30 | 30 | 30 | 30 | 30 | 30 | 30 | 30 |
|  | Stabilizer A |  |  |  | 0.6 | 0.6 | 0.4 | 0.4 | 0.4 | 0.6 | 0.4 |
|  | Stabilizer B |  |  |  |  |  | 0.2 |  |  | 0.6 | 0.8 |
|  | Stabilizer C |  |  |  |  |  |  | 0.2 |  |  |  |
|  | Stabilizer D |  |  |  |  |  |  |  | 0.2 |  |  |
|  | Organic polyisocyanate | 106 | 106 | 106 | 106 | 106 | 106 | 106 | 106 | 106 | 106 |
| GC/ (ppm) | Immediately after foaming HCFC-1131a | 115 | 0 | 0 | 0 | 0 | 0 | 0 | 0 | 0 | 0 |
|  | HCFC-151a | 50 | 65 | 70 | 0 | 0 | 0 | 0 | 0 | 0 | 0 |
|  | 90° C. × 1 week HCFC-1131a | 16000 | 305 | 310 | 330 | 300 | 290 | 280 | 300 | 290 | 280 |
|  | HCFC-151a | 335 | 390 | 505 | 17 | 10 | 0 | 0 | 0 | 0 | 0 |

According to each foaming formulation given in Table 1, the raw materials were adjusted to a temperature of 20±1° C. and then mixed up together by stirring at a high speed for 5 seconds for allowing the reaction to proceed. After foaming, the concentrations of gaseous components in the rigid polyurethane foam produced were determined by conventional gas chromatography.

As the results of Comparative Example 1 indicate, high levels of HCFC-1131a and HCFC-151a were detected in rigid polyurethane foams produced by the conventional method using HCFC-141b as the blowing agent upon gas analysis immediately after foaming and after one-week standing of the foams at 90° C.

On the contrary, as the results of Comparative Examples 2 and 3 indicate, the use, as the catalyst, of an organic metal catalyst and/or an imidazole compound catalyst results in very much reduced levels of formation of HCFC-1131a.

Furthermore, as the results of Examples 1 to 7 indicate, the combined use of a stabilizer can suppress the formation of HCFC-151a as well.

We claim:

1. A method of producing rigid polyurethane foams which comprises reacting a polyol with a polyisocyanate selected from the group consisting of an organic polyisocyanate and an organic polyisocyanate prepolymer for foaming in the presence of 1,1-dichloro-1-fluoroethane as the blowing agent and a stabilizer which inhibits decomposition of 1,1-dichloro-1-fluoroethane remaining in said polyurethane foams and in the presence of an organic metal-catalyst and/or an imidazole compound catalyst.

2. The method of claim 1 wherein the polyol is selected from among polyether polyols containing 2 to 8 functional groups and having a hydroxyl value of 300 to 600 mg KOH/g, polyester polyols containing 2 to 4 functional groups and having a hydroxyl value of 250 to 500 mg KOH/g and phenol resins containing reactive methylol groups.

3. The method of claim 2 wherein the polyol is a polyether polyol derived from at least one of trimethylolpropane, sorbitol, o-tolylenediamine and m-tolylenediamine by addition of at least one of ethylene oxide and propylene oxide, said polyol having a hydroxyl value of 300 to 600 mg KOH/g.

4. The method of claim 1 wherein the organic polyisocyanate is a polymethylenepolyphenyl isocyanate of the general formula

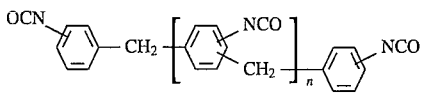

(wherein n is an integer of 0 to 6) and/or tolylene diisocyanate.

5. The method of claim 1 wherein the organic polyisocyanate is a prepolymer derived from a polymethylenepolyphenyl isocyanate of the general formula

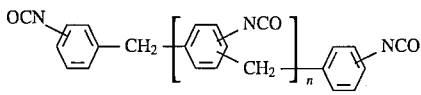

(wherein n is an integer of 0 to 6) and/or tolylene diisocyanate and a hydroxyl-containing compound.

6. The method of claim 5 wherein the hydroxyl-containing compound is at least one member selected front the group consisting of monohydric alcohols containing one functional group and having a molecular weight of 32 to 300, phenols containing one functional group and having a molecular weight of 32 to 300 and polyols containing 2 or 3 functional groups and having a molecular weight of 62 to 600.

7. The method of claim 6 wherein the hydroxyl-containing compound is at least one member selected from the group consisting of methanol, ethanol, n- butanol, ethylene glycol monomethyl ether, diethylene glycol monomethyl ether, phenol, o-, m-, p-cresol, ethylene glycol, diethylene glycol, propylene glycol, 1,4-butanediol, 1,6-hexanediol, glycerol, trimethylolpropane, bi- or tri-functional polyether polyols and bi- or trifunctional polyester polyols.

8. The method of claim 1 wherein the blowing agent 1,1-dichloro-1-fluoroethane is used in an amount of 1 to 100% on the polyol weight basis.

9. The method of claim 1 wherein the stabilizer is at least one member selected from the group consisting of nitro compounds, such as nitroalkanes, nitrobenzene, dinitrobenzene, trinitrobenzene, halogenated nitrobenzene, nitroanisole, nitrostyrene, nitrophenol and nitrocatechol; alkenyl compounds containing at least one double bond, such as hexadiene, allene, butadiene, isoprene, pentadiene, β-myrcene, isopropenyltoluene, diisopropenylbenzene and alloocimene; epoxy-containing compounds, such as 1,2-butylene oxide, isobutylene oxide, glycidyl allyl ether, glycidyl phenyl ether, glycidyl p-isopropenylphenyl ether, glycidyl p-nitrophenyl ether, 1,3-butadienyl glycidyl ether, glycidyl acrylate, glycidyl furancarboxylate and N,N-diglycidylaniline; acrylic acid esters and methacrylic acid esters, such as 2-hydroxyethyl methacrylate, diethylene glycol monomethyl methacrylate and methoxypolyethylene glycol monoethyl methacrylate; and phenols, such as 2,6-di-tert-butyl-p-cresol, thymol, p-tert-butylphenol, eugenol, isoeugenol, butylated hydroxyanisole, tert-butylcatechol and 2,5-di-tert-butylhydroquinone.

10. The method of claim 1 wherein the stabilizer is used in an amount of 0.1 to 10% on the blowing agent weight basis.

11. The method of claim 10 wherein the stabilizer is used in an amount of 0.3 to 6% on the blowing agent weight basis.

12. The method of claim 1 wherein the proportions of the polyol and organic polyisocyanate are such that the NCO/OH equivalent ratio is within the range of 1.0 to 3.0.

13. The method of claim 1 wherein the organic metal catalyst is at least one member of the class consisting of stannous octoate, dibutyltin dilaurate and lead octylate.

14. The method of claim 1 wherein the imidazole compound catalyst is at least one member selected from the group consisting of imidazole, 1-methylimidazole, 1,2-dimethylimidazole, 1-methyl-2-propylimidazole, 1-methyl-2-isobutylimidazole and 1-n-butyl-2-methyl imidazole.

15. The method of claim 1 wherein the catalyst is used in an amount of 0.01 to 20% on the organic polyisocyanate weight basis.

16. A rigid polyurethane foam obtained by reacting a polyol with an organic polyisocyanate for foaming in the presence of 1,1-dichloro-1-fluoroethane as the blowing agent and a stabilizer therefor and in the presence of an organic metal catalyst and/or an imidazole compound catalyst.

* * * * *

UNITED STATES PATENT AND TRADEMARK OFFICE
CERTIFICATE OF CORRECTION

PATENT NO. : 5,561,172
DATED : October 1, 1996
INVENTOR(S) : OMURE et al

It is certified that error appears in the above-indentified patent and that said Letters Patent is hereby corrected as shown below:

Title page: item (73) should read as follows:

(73) Assignee: Daikin Industries, Ltd., Osaka, Japan and Takeda Chemical Industries, Ltd., Osaka, Japan Signed and Sealed this Third Day of June, 1997

Attest:

BRUCE LEHMAN

*Attesting Officer*     *Commissioner of Patents and Trademarks*